United States Patent [19]

Jones et al.

[11] 3,947,557

[45] Mar. 30, 1976

[54] ZINC COMPLEXES OF BASIC ALUMINUM BROMIDES AND METHODS OF MAKING SAME

[75] Inventors: John L. Jones, North Plainfield; Andrew M. Rubino, New Providence, both of N.J.; Charles B. Lindahl, Sand Springs, Okla.

[73] Assignee: Armour Pharmaceutical Company, Chicago, Ill.

[22] Filed: June 3, 1975

[21] Appl. No.: 583,381

Related U.S. Application Data

[62] Division of Ser. No. 164,433, July 20, 1971.

[52] U.S. Cl. .................. 423/463; 423/463; 424/47
[51] Int. Cl.$^2$.. C01G 25/04; C01F 7/00; C01F 7/48; C01G 9/04
[58] Field of Search ............................ 423/463, 462

[56] References Cited
UNITED STATES PATENTS

| | | | |
|---|---|---|---|
| 2,854,382 | 9/1958 | Grad | 424/68 X |
| 2,906,668 | 9/1959 | Beekman | 423/463 X |
| 3,405,153 | 10/1968 | Jones et al. | 423/463 X |

*Primary Examiner*—Edward Stern
*Attorney, Agent, or Firm*—Seidel, Gonda & Goldhammer

[57] ABSTRACT

Alcohol soluble complexes of basic aluminum bromides may be prepared by adding zirconyl or zinc bromide or chloride, or zirconyl hydroxychloride or hydroxybromide, or mixtures of the above chlorides and bromides to an aqueous solution of five-sixths basic aluminum bromide, and drying the resulting mixture to a substantially friable solid, such as by vacuum or spray drying. The complexes preferably have an Al/Zn or Al/Zr mol ratio of about 3:1 to 20:1, and the complex solids preferably contain about 15 to 30 weight percent water by Karl Fischer analysis. Such complex solids have a high degree of solubility in anhydrous alcohol and a high compatibility with halogenated hydrocarbons. These properties make the complexes suitable for aerosol formulations and particularly antiperspirant compositions.

9 Claims, No Drawings

ZINC COMPLEXES OF BASIC ALUMINUM BROMIDES AND METHODS OF MAKING SAME

This application is a division of our copending application Ser. No. 164,433, filed July 20, 1971, entitled "Zirconium Complexes Of Basic Aluminum Bromides And Methods Of Making Same".

The present invention relates to zinc and zirconium complexes of basic aluminum bromides and methods of making such complexes. More particularly, the invention is directed to complexes of five-sixths basic aluminum bromides and chlorides and/or bromides of zinc and zirconyl, which complexes are particularly suitable for use in antiperspirant compositions.

It has been known in the art for some time that aluminum compounds are among the most useful active ingredients in astringent or antiperspirant compositions and other cosmetic products. Of particular interest in this regard are the basic aluminum halides.

It is also known that zinc salts and zirconium salts, such as zirconyl chloride ($ZrOCl_2$ or zirconium oxychloride) are capable of preventing or retarding the exudation of perspiration from the skin and have been used or suggested for use in antiperspirant compositions. However, the usual zirconium salts are strongly acidic, and thus are generally not usable due to irritation of the skin and damage to clothing. Furthermore, salts of weak acids are relatively ineffective in inhibiting the flow of perspiration.

A number of solutions have been proposed to the above problems in the form of complexes which include zinc or zirconium salts and aluminum hydroxyhalides. Examples of such complexes are described in U.S. Pat. Nos. 2,814,584 and 2,814,585 for "BUFFERED ANTIPERSPIRANT COMPOSITIONS" issued to Edwin William Daley, which disclose aqueous solutions of zirconium and/or hafnium salts which are buffered with basic aluminum halides or nitrates and amino acids to render the solutions safe for antiperspirant usage. Another example is U.S. Pat. No. 2,906,668 for "ZIRCONYL AND ALUMINUM HALOHYDROXY COMPLEX" issued to Stewart M. Beekman, which discloses aqueous solution complexes of zirconyl halides with aluminum hydroxyhalides and a method for maintaining a high solution pH and preventing gelling.

The complexes produced according to the above patents suffer from the disadvantage of being in aqueous solutions. Thus, in order to be commercially acceptable for use in present day aerosol antiperspirant compositions, it is generally necessary that the astringent compositions meet the following requirements:

1. The composition should contain a minimal amount of water so as to avoid corrosion of metal values and containers for the product, and thereby eliminate product contamination resulting from the corrosion;
2. The composition must be compatible with the halogenated hydrocarbons which are conventionally employed as propellants in aerosol antiperspirant sprays; and
3. The active ingredient must be capable of being dissolved in non-aqueous media (e.g., anhydrous alcohol) in concentrations of at least 10 percent by weight (5 percent by weight in aerosol formulations, which generally contain about 40 to 60 percent volatile propellants).

More recently, complexes meeting the above criteria have been developed which contain a zinc or zirconyl halide or hydroxyhalide, a basic aluminum halide, and a polyhydroxy compound having at least 2 carbon atoms to which are attached at least 2 hydroxy groups. Such complexes are described in U.S. pat. No. 3,405,153 for "Metal-Aluminum Inorganic-Organic Complexes And Methods Of Preparing Same" issued to John L. Jones and Andrew M. Rubino, and assigned to the same assignees as the present invention. Nevertheless, the present invention represents further attempts to produce even better astringent aluminum compounds.

Accordingly, it is an object of the present invention to provide an aluminum compound having a high degree of solubility in anhydrous alcohol and excellent compatibility with conventional aerosol propellants.

It is a further object of the present invention to provide improved complexes of zinc and zirconium salts with basic aluminum bromides, which complexes possess good antiperspirant properties.

It is another object of the present invention to provide a method for preparing improved complexes of zinc and zirconium salts with basic aluminum bromides.

Still another object of the present invention is the provision of complexes of zinc or zirconyl halides or hydroxyhalides with five-sixths basic aluminum bromides, which complexes are highly soluble in anhydrous alcohol and highly compatible with aerosol propellants so as to be suitable for usage in aerosol antiperspirant compositions.

Still further objects will appear hereinafter.

The above and other objects are achieved by the complexes of the present invention which are prepared by providing an aqueous solution of five-sixths basic aluminum bromide; mixing with the aqueous solution a compound selected from the group consisting of zinc chloride, zinc bromide, zirconyl chloride, zirconyl bromide, zirconyl hydroxychloride, zirconyl hydroxybromide, and mixtures of these compounds; and drying the resulting mixture to produce the complex in the form of a substantially friable solid.

The alcohol soluble complex solids of the present invention may be represented by the following general empirical formula:

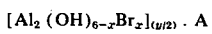

in which $x$ = about 0.9 to 1.2, $y$ = about 3 to 20, A is a compound selected from the group consisting of zinc chloride, zinc bromide, zirconyl chloride, zirconyl bromide, zirconyl hydroxychloride, zirconyl hydroxybromide, and mixtures of these compounds.

Thus, in the case of the zinc derivatives, the generalized formula will be:

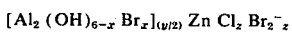

in which $x$ and $y$ are as above and $z$ = 0 to 2.

In the case of the zirconyl compounds there is a continuous range of possible values of hydroxy and halide (X) proportions, ranging from zirconyl halide (X/Zr = 2.0) to zirconyl hydroxyhalide (X/Zr = 1.0), since the starting zirconium material is not necessarily a pure compound. When the complex is prepared from zirconium carbonate and the hydrohalide, the ratio can of course be adjusted as desired. Also, it is possible to prepare a mixture of halides having more desirable properties. Accordingly, the generalized formula for the zirconium complex is:

$$[Al_2(OH)_{6-x} Br_x]_{(y/2)} \cdot ZrO(OH)_{2-z} X_z$$

in which $x$ and $y$ are as above, $z$ = about 0.9 to 2, and X = Br or Cl.

It will be understood that the above formulas are greatly simplified and are intended to include basic aluminum bromides containing coordinated or bound molecules of water. The preferred solid complexes of the present invention will have a water content (both free and bound water) of about 15 to 30 weight percent based on the total weight of the solid and determined by Karl Fischer titration.

It should be emphasized that the 15 to 30 weight percent range of water contents is probably somewhat higher than the actual value, since values obtained with the Karl Kischer method are generally higher than obtained by calculation from assays for the metals and halides in the complexes. However, in the presence of aluminum, the assays for zinc and zirconium are somewhat uncertain, and therefore Karl Fischer values are used throughout the application rather than calculated values.

The basic aluminum bromide compounds suitable for use in the preparation of the complexes of the present invention include those having one or more units of the general formula:

$$Al_2(OH)_{6-x} Br_x$$

wherein $x$ may vary from about 0.9 to about 1.2. The approximately 5/6 basic aluminum bromides of the above formula have an aluminum to bromine ratio (Al/Br mol ratio) of about 1.8 to 2.1.

It should be understood that the above formula is greatly simplified and is intended to include simple hydrated salts, polymers and other complexes or mixtures, such that the basic formula would be an average consisting of full and/or fractional units. Examples of such basic aluminum bromides are described in copending application Ser. No. 88,206 of John L. Jones and Andrew M. Rubino, filed Nov. 9, 1970, for "Basic Aluminum Bromide Compositions," and assigned to the same assignees as the present invention.

The basic aluminum bromides used in the present invention may be prepared in a manner analogous to the conventional production of aluminum chlorhydroxide by reacting aluminum metal with the hydrobromic acid in water solution, or by reacting aluminum metal with a water solution of aluminum bromide. In addition, they may be prepared by reacting elemental bromine with aluminum metal in a water medium. Such preparations are described in more detail in copending application Ser. No. 88,206.

The first step of the method of the present invention comprises the formation of an aqueous solution of a basic aluminum bromide. This may be conveniently achieved simply by using the filtered aqueous product obtained from any of the above-described preparations. The aluminum to bromine mol ratio may be suitably adjusted during any of these preparations. Alternatively, the aqueous basic aluminum bromide solution could be prepared from a solid basic aluminum bromide having the desired Al/Br mol ratio, since such solids are readily soluble in water.

The exact concentration of the aqueous basic aluminum bromide solution is not critical and may vary over a considerable range. However, too much water is uneconomical due to the necessity of removing the excess water during the drying step, and too little may hinder the preparation of the product due to increased viscosity. A suitable aqueous solution contains about 50 weight percent of the basic aluminum bromide.

The zinc or zirconium compounds may be added to the aqueous basic aluminum bromide solution in any convenient manner or form. For example, the zinc chloride ($ZnCl_2$) or zinc bromide ($ZnBr_2$) may be added in their dry crystalline form or as an aqueous solution. The zinc halides may also be easily and relatively cheaply prepared by dissolution of zinc or zinc oxide in hydrochloric acid or hydrobromic acid.

The zirconium compounds are suitably added in the form of aqueous solutions, which preferably contain about 5 to 25 weight percent zirconium. Zirconyl chloride (basic zirconium chloride or zirconium oxychloride) and zirconyl hydroxychloride solution are commercially available. In the alternative, the zirconium compounds can be made by dissolution of commercially available zirconium carbonate paste (carbonated hydrous zirconia) in the appropriate amount of the halogen acid.

The addition of the zinc or zirconium compound to the aqueous basic aluminum bromide solution is by simple mixing, and contrary to the methods described in U.S. Pat. Nos. 2,906,668 and 3,405,153, discussed above, heating or extended agitation is not generally required. Although heating to a temperature near reflux (100° C), as in Example VII, may be used where desired, most gelatin problems which may occur where the zirconium compounds are added may generally be avoided by dilution of the mixture with water. The zinc salts are miscible under all conditions, but there is usually a decrease in pH on standing or heating. However, to date there is no significant evidence that heating or standing adversely affects any of the dried products.

The amount of the particular zinc or zirconium compound added to the aqueous bromide solution is also not particularly crucial, and may vary over a wide range. Preferred aluminum to zirconium or aluminum to zinc mol ratios (hereinafter referred to as Al/Zr and Al/Zn ratios) range between about 3 and 20 (i.e., y in the previously discussed formulas equal about 3 to 20). There is of course no reason that y could not be greater than 20, however such complexes would merely be approaching the pure basic aluminum bromides. Also, products having ratios lower than about 3 can be made, but with less satisfactory results. Thus, with Al/Zr ratios lower than 3 there are more gelation problems and the products are more acidic, while with Al/Zn ratios lower than 3 there is a tendency to increase the hygroscopicity of the dried product, which would yield undesirable commercial characteristics.

It will be obvious to one of ordinary skill in the art that the amount of zinc or zirconium compound to be added to the aqueous bromide solution will depend upon the particular zinc or zirconium compound being added and the desired amount of zinc or zirconium in the final product.

After the addition of the desired zinc or zirconium compound, the resulting solution mixture is dried to form a friable solid complex having the desired water content. Almost any of the usual drying methods known in the art are acceptable, such as air drying at atmospheric temperature and pressure, vacuum drying, freeze drying and spray drying. Rotary vacuum drying at a maximum temperature of about 40°C and about 15 millimeters of mercury has been particularly satisfactory, but spray drying is probably the most practical and economical from a commercial standpoint. The drying conditions for spray drying will vary greatly and depend to a large extent on the particular spray drying apparatus employed, suitable conditions for each apparatus being readily determinable by one of ordinary skill in the art.

Although the particular quantity of water present in the final solid complex is not critical, lower water contents are of course preferred. However, care must be exercised to prevent the product from becoming over-dried to the point of alcohol insolubility. A suitable range of water contents is about 15 to 30 weight percent as determined by Karl Fischer analysis and based on the total weight of the complex solid. But as mentioned above, the actual range of water content in the dried product will probably be somewhat lower.

A typical preferred solid product of the present invention will have an assay within the following approximate ranges:

12–20% aluminum
3–14% zinc or zirconium
Al/Zn or Al/Zr ratio = 3–20
15–30% water by Karl Fischer Throughout the application all percentages are given as weight percents based on the total weight of the complex solid, unless otherwise specified. The percentages of metal and halide are determined by assays by accepted analytical procedures.

The dried solid complexes of the present invention show excellent alcohol solubility. For example, virtually all of the products are soluble in anhydrous (SDA-40) alcohol within about one hour or less to the extent of at least about 30 weight percent.

Furthermore, the solid complexes of the present invention have excellent compatibility with the halogenated hydrocarbons, such as those conventionally used as aerosol propellants. As has become standard in the art, halohydrocarbon compatibility in the present application is measured on the basis of the number of cc's of $CCl_4$ which may be admixed with 60 grams of a 30 weight percent solution of the complex in SDA-40 alcohol before a permanent cloudiness or haze occurs. The products of the present invention generally exhibit a $CCl_4$ compatibility of at least 100 cc's $CCl_4$ and up to 250 or more CC's $CCl_4$.

Although the halohydrocarbon compatibility will vary somewhat depending upon whether zinc or zirconium compounds are used in forming the complexes, the values for both zinc and zirconium complexes compare quite favorably with compatibility values for the pure basic aluminum bromides. Thus, the zirconium complexes generally have $CCl_4$ compatibilities in the range of about 150 to 250 or more, while the zinc complexes generally have $CCl_4$ compatibilities of about 100 to 200. As a comparison the $CCl_4$ compatibilities of the pure basic aluminum bromides, such as illustrated in copending application Ser. No. 88,206 are comparable to or slightly higher than the values for the zinc complexes.

Finally, the pH values for the complex solids of the present invention are generally higher, and therefore more desirable, than the zirconyl complexes described in U.S. Pat. Nos. 2,906,668 and 3,405,153, discussed previously. For example, the zirconyl polyol derivatives of the basic aluminum chlorides described in U.S. Pat. No. 3,405,153 generally produced alcoholic pH values (i.e., determined on the basis of the 30 weight percent solution of the complex in SDA-40 alcohol) ranging from about 0.3 to 0.9. On the other hand, the solid complexes of the present invention generally yield alcoholic pH's in the range of about 0.9 to 2.6. In particular, the pH's of the complexes of the present invention are generally inversely related to the halohydrocarbon compatibility. Thus, the zirconyl chloride or bromide complexes, which are the most compatible, have a pH range of about 0.9 to 1.4; the zirconyl hydroxychlorides or hydroxybromides have a pH range from about 1.5 to 2.5; and the zinc chlorides or bromides, which have the lowest compatibility, have a pH range from about 2.4 to 2.6. Such pH ranges are to be preferred over the previous zirconyl complexes due to the potential reduction of corrosion problems and perfume deterioration in antiperspirant compositions employing the complexes.

The alcohol soluble zinc and zirconium complexes of basic aluminum bromides and the methods of making the solid complexes of the present invention will now be described in more detail with reference to the following specific, non-limiting examples:

EXAMPLE I 404 gm of zirconyl hydroxybromide (21.7% Zr) was added to 1,428 gm of 50% basic aluminum bromide (10.9% Al) giving an Al/Zr ratio of 6.0:1. The solution was spray dried at an outlet temperature of 180°F. The product dissolved in anhydrous SDA-40 in about an hour to form a 30% solution with a $CCl_4$ compatibility of 198 cc. Analysis: 15.8% Al, 9.1% Zr, 30.6% Br, 18.9% $H_2O$ by Karl Fischer.

EXAMPLE II 227 gm of zirconyl hydroxybromide (21.7% Zr) was added to 1,336 gm of 50% basic aluminum bromide (10.9% Al) giving an Al/Zr ratio of 10.0:1. The solution was spray dried at an outlet temperature of 180°F. The product dissolved in anhydrous SDA-40 in about an hour to form a 30% solution with a $CCl_4$ compatibility of 190 cc. Analysis: 17.3% Al, 6.2% Zr, 31.1% Br, 18.7% $H_2O$ by Karl Fischer.

EXAMPLE III

To 73.9 gm of 50% basic aluminum bromide (11.8% Al) was added 39.5 gm of zirconyl hydroxybromide (21.7% Zr) giving an Al/Zr ratio of 3.4:1. After overnight stirring, the solution was dried in a rotary vacuum evaporator at 30°C. and about 15 mm Hg. The product dissolved in anhydrous SDA-40 in less than an hour to form a 30% solution with a $CCl_4$ compatibility of 162 cc. Analysis: 13.2% Al, 13.0% Zr, 28.7% Br, 22.6% $H_2O$ by Karl Fischer.

EXAMPLE IV 28 gm of zirconyl bromide (13.3% Zr) was added to 100.2 gm of 50% basic aluminum bromide (11.3% Al) giving an Al/Zr ratio of 9.1:1. After overnight stirring, 106 gm of the solution was dried in a rotary vacuum evaporator at 30°C. and about 15 mm Hg to 60 gm. The product dissolved in anhydrous SDA-40 in less than 0.3 hour to form a 30% solution with a $CCl_4$ compatibility of 253 cc. Analysis: 16.1% Al, 5.7% Zr, 35.1% Br, 21.3% $H_2O$ by Karl Fischer.

EXAMPLE V 29.8 gm of zirconyl bromide (13.3% Zr) was added to 64.1 gm of 50% basic aluminum bromide (11.3% Al) giving an Al/Zr ratio of 5.5:1. After overnight stirring, 68 gm of the solution was dried in a rotary vacuum evaporator at 30°C. and about 15 mm Hg to 38 gm. The product dissolved in anhydrous SDA-40 in about 0.4 hour to form a 30% solution with a $CCl_4$ compatibility of 251 cc. Analysis: 13.8% Al, 8.0% Zr, 35.1% Br, 22.7% $H_2O$ by Karl Fischer.

EXAMPLE VI

To 88.1 gm 50% basic aluminum bromide (11.2% Al) was added 22.2 gm of zirconyl hydroxychloride (20.2% Zr) giving an Al/Zr ratio of 10.0:1. The solution was dried in a rotary vacuum evaporator at 30°C. and about 15 mm Hg to 50 gm. The product dissolved in anhydrous SDA-40 to form a 30% solution with a compatibility of 173 cc. Analysis: 18.1% Al, 6.2% Zr, 18.4% $H_2O$ by Karl Fischer.

EXAMPLE VII

To 60.5 gm 50% basic aluminum bromide (11.1% Al) was added 26.4 gm of zirconyl hydroxychloride (20.2% Zr) giving an Al/Zr ratio of 6.0:1. After mixing, the solution started to gel. This was broken up by heating for about 2 hours. After overnight stirring, 59.2 gm of the solution was dried to 28.8 gm in a rotary vacuum evaporator at 30°C. and about 15 mm Hg. The product dissolved in anhydrous SDA-40 in 35 minutes to form a 30% solution with a compatibility of 197 cc. Analysis: 16.3% Al, 9.7% Zr, 23.2% $H_2O$ by Karl Fischer.

EXAMPLE VIII 43.1 gm of zirconyl chloride (8.6% Zr) was added to 91.7 gm of 50% basic aluminum bromide (11.3% Al) giving an Al/Zr ratio of 9.4:1. After overnight stirring, 95.2 gm of the solution was dried in a rotary vacuum evaporator at 30°C. and about 15 mm Hg to 49.4 gm product. The product dissolved in anhydrous SDA-40 in less than 0.3 hour to form a 30% solution with a compatibility of 199 cc. Analysis: 15.7% Al, 5.4% Zr, 28.8% $H_2O$ by Karl Fischer.

EXAMPLE IX 56.3 gm of zirconyl chloride (8.6% Zr) was added to 72.7 gm of 50% basic aluminum bromide (11.3% Al) giving an Al/Zr ratio of 5.7:1. After overnight stirring, 102.8 gm solution was dried in a rotary vacuum evaporator at 30°C. and about 15 mm Hg to give 46.8 gm product. The product dissolved in anhydrous SDA-40 in less than 0.75 hour to form a 30% solution with a $CCl_4$ compatibility of 232 cc. Analysis: 14.1% Al, 8.2% Zr, 27.3% $H_2O$ by Karl Fischer.

EXAMPLE X

To 1,282 gm of 50% basic aluminum bromide (10.7% Al) was added 114.4 gm of zinc bromide giving an Al/Zn ratio of 10.0:1. The solution was spray dried using an outlet temperature of 180°F. The product dissolved in anhydrous SDA-40 in about an hour to form a 30% solution with a $CCl_4$ compatibility of 176 cc. Analysis: 17.8% Al, 4.2% Zn, 16.8% $H_2O$ by Karl Fischer.

EXAMPLE XI

To 54.8 gm of 50% basic aluminum bromide (11.8% Al) was added 13.7 gm of $ZnBr_2$ giving an Al/Zn ratio of 3.9:1. After overnight stirring, 66.8 gm of the solution was dried in a rotary vacuum evaporator at 30°C. and about 15 mm Hg to give 44 gm product. The product dissolved in anhydrous SDA-40 in less than 15 minutes to form a 30% solution with a compatibility of 137 cc. Analysis: 14.1 % Al, 8.5% Zn, 16.2% $H_2O$ by Karl Fischer.

EXAMPLE XII 4.3 gm of $ZnCl_2$ was added to 77.8 gm of 50% basic aluminum bromide (11.2% Al) giving an Al/Zn ratio of 10.3:1. The solution was dried in a rotary vacuum evaporator at 30°C. and about 15 mm Hg. The product dissolved in anhydrous SDA-40 overnight to form a 30% solution with a $CCl_4$ compatibility of 146 cc. Analysis: 19.3% Al, 4.6% Zn, 15.5% $H_2O$ by Karl Fischer.

EXAMPLE XIII 8.5 gm of $ZnCl_2$ was added to 5.7 gm of 50% basic aluminum bromide (11.8% Al) giving an Al/Zn ratio of 4.1:1. After overnight stirring, 63.7 gm of solution was dried in a rotary vacuum evaporator at 30°C. and about 15 mm Hg to 40 gm. The product dissolved in anhydrous SDA-40 in about 0.3 hour to form a 30% solution with a $CCl_4$ compatibility of 116 cc. Analysis: 16.4% Al, 9.7% Zn, 15.5% $H_2O$ by Karl Fischer.

The complexes of the present invention are useful in antiperspirant and other cosmetic applications, and particularly aerosol antiperspirant sprays. Such aerosol antiperspirant formulations comprise a non-toxic dermatologically acceptable nonaqueous solvent, such as anhydrous ethanol, and about 40 to 60 weight percent of a fluorocarbon propellant such as Freon 12, Freon 114, Freon 22, Freon 113, etc. Other suitable solvents and propellants will be readily apparent to one of ordinary skill in the art. For example, a list of suitable substitutes is presented in column 9 of U.S. Pat. No. 3,405,153. The solid complexes should be present to the extent of at least 5 weight percent of the total aerosol formulation. Since the volatile propellants are dissipated immediately upon application, such a concentration will yield an effective concentration of at least 10 weight percent based on the non-aqueous solvent. Of course, due to the excellent carbon tetrachloride compatibilities of the complexes of the present invention, even higher concentrations may be used, thus yielding higher concentrations of the active ingredients.

As examples of aerosol antiperspirant formulations, four batches were prepared using the complexes prepared according to Examples I, VI, XI and XIII above. The four batches are listed below in Table I.

TABLE I

| Components of Formulation Examples Complex from Example: | Weight Percentages of Each Component | | | |
|---|---|---|---|---|
| | I | VI | XI | XIII |
| Concentration of Complex | 11.0 | 9.0 | 7.0 | 7.0 |
| Stearic Acid | 2.0 | 1.0 | 1.0 | 1.0 |
| Hexadecyl Alcohol | 1.0 | | | 1.0 |

TABLE I-continued

| Components of Formulation Examples Complex from Example: | Weight Percentages of Each Component | | | |
|---|---|---|---|---|
| | I | VI | XI | XIII |
| Silicone Fluid 1066 (General Electric) | 1.0 | | 1.0 | 1.0 |
| Isopropyl Myristate | | 1.0 | 1.0 | |
| SDA-40 Alcohol | 35.0 | 39.0 | 40.0 | 40.0 |
| Dichlorotetrafluoroethane | 30.0 | 30.0 | 30.0 | 30.0 |
| Dichlorodifluoromethane | 20.0 | 20.0 | 20.0 | 20.0 |

All four of the formulations shown in Table I exhibited good stability (i.e. lack of gelation tendencies) after one week at ambient temperatures.

The present invention may be embodied in other specific forms without departing from the spirit or essential attributes thereof and, accordingly, reference should be made to the appended claims, rather than to the foregoing specification as indicating the scope of the invention.

We claim:

1. A method of preparing alcohol soluble solid complexes of five-sixths basic aluminum bromides comprising the steps of providing an aqueous solution of five-sixths basic aluminum bromide having the general empirical formula:

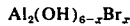

in which $x$ equals about 0.9 to 1.2; adding to said aqueous solution a substance selected from the group consisting of zinc chloride, zinc bromide, and combinations of either or both of said zinc halides with zirconyl chloride, zirconyl bromide, zirconyl hydroxychloride and/or zirconyl hydroxybromide; and drying the resulting mixture to a substantially friable solid.

2. Alcohol soluble complex solids formed by the method of claim 1.

3. A method according to claim 1 wherein said mixture is dried to a water content of about 15 to 30 weight percent determined by Karl Fischer analysis and based on the total weight of the solid.

4. A method according to claim 1 wherein said mixture is vacuum dried at a maximum temperature of about 40° C.

5. A method according to claim 1 wherein said mixture is spray dried.

6. Alcohol soluble complexes of five-sixths basic aluminum bromides formed by the method of claim 1 wherein the Al/Zn or Al/Zr mol ratio is about 3:1 to 20:1.

7. Alcohol soluble complexes of five-sixths basic aluminum bromides formed by the method of claim 1 and having a halohydrocarbon compatibility of at least 100 cc's of $CCl_4$, when the $CCl_4$ is admixed with 60 grams of a 30 weight percent solution of said complex in SDA-40 alcohol, before a permanent cloudiness occurs.

8. Alcohol soluble complexes of five-sixths basic aluminum bromides formed by the method of claim 3.

9. Alcohol soluble complex solids according to claim 2 wherein said solids have a water content of about 15 to 30 weight percent determined by Karl Fischer analysis and based on the total weight of the solid.

* * * * *